United States Patent [19]
Suhocki et al.

[11] Patent Number: 5,643,281
[45] Date of Patent: Jul. 1, 1997

[54] DEVICES FOR REMOVING FIBRIN SHEATHS FROM CATHETERS

[75] Inventors: Paul V. Suhocki; Mark T. Ridinger, both of Durham, N.C.

[73] Assignee: Duke University, Durham, N.C.

[21] Appl. No.: 417,019

[22] Filed: Apr. 5, 1995

[51] Int. Cl.$^6$ .................................................. A61B 17/22
[52] U.S. Cl. ........................... 606/113; 606/106; 606/127
[58] Field of Search ............................ 606/106, 110, 606/113, 114, 119, 127, 128; 604/52; 128/898

[56] References Cited

U.S. PATENT DOCUMENTS

| | | |
|---|---|---|
| 798,839 | 9/1905 | Stowe . |
| 1,772,352 | 8/1930 | Huber . |
| 3,791,387 | 2/1974 | Itoh . |
| 4,568,338 | 2/1986 | Todd . |
| 4,694,838 | 9/1987 | Wijayarthna . |
| 4,738,667 | 4/1988 | Galloway . |
| 4,927,426 | 5/1990 | Dretler . |
| 5,071,649 | 12/1991 | Hunter . |
| 5,084,054 | 1/1992 | Bencini et al. ............... 606/127 |
| 5,098,441 | 3/1992 | Wechler . |
| 5,108,420 | 4/1992 | Marks . |
| 5,171,233 | 12/1992 | Amplatz et al. . |
| 5,192,286 | 3/1993 | Phan et al. . |
| 5,207,687 | 5/1993 | Bernon ............................ 606/119 |
| 5,290,229 | 3/1994 | Paskar . |
| 5,330,482 | 7/1994 | Gibbs et al. . |
| 5,341,815 | 8/1994 | Cofone et al. . |

FOREIGN PATENT DOCUMENTS

| | | | |
|---|---|---|---|
| 958331 | 2/1957 | Germany ............................ 606/106 |
| 140158 | 4/1960 | U.S.S.R. ............................. 606/113 |
| 1683701 | 10/1991 | U.S.S.R. ............................. 606/113 |

OTHER PUBLICATIONS

The Retriever—Endovascular Snare by Target Therapeutics, Aug. 27, 1992.

Primary Examiner—Robert A. Hafer
Assistant Examiner—Benjamin Koo
Attorney, Agent, or Firm—Nixon & Vanderhye P.C.

[57] ABSTRACT

Medical devices have a snare loop for removing patient-internal material, for example, a fibrin sheath which may form at the distal end of a venous catheter, and may be inserted intraluminally through the catheter during a medical procedure. The snare loop is capable of retroflexing in a proximal direction when extended beyond the distal end of the catheter so that the snare loop encircles the catheter's distal region. Such retroflexing may be accomplished by incorporating at least one pair of bend regions in the guide wire which are axially spaced-apart from one another. These bend regions will cause the shape-memory guide wire to flex upon advancement of the device beyond the distal end of the venous catheter so that the snare loop is capable of retroflexing around the catheter's distal end. Alternatively, a number of proximally directed struts having one end attached to the distal end of the guide wire. A draw wire extends from the guide catheter and is flexed in a proximal direction so as to be connected to the snare loop which is positionally held by the terminal ends of the struts. A membrane may optionally be connected to the struts so that the removed fibrin sheath segment may be captured and removed proximally through the lumen of the implanted catheter.

17 Claims, 4 Drawing Sheets

DEVICES FOR REMOVING FIBRIN SHEATHS FROM CATHETERS

RELATED APPLICATIONS

This application may be deemed to be related to U.S. patent application Ser. No. 08/417,018, now U.S. Pat. No. 5,556,380, filed even date herewith in the name of the same inventors as the present application, the entire content of which is expressly incorporated hereinto by reference.

FIELD OF INVENTION

The present invention relates generally to the field of medical devices. More particularly, the present invention relates to the field of snares used during medical procedures to remove material from a patient. In its preferred embodiments, the present invention is especially adapted to remove fibrin sheaths from the distal ends of intravascular catheters.

BACKGROUND AND SUMMARY OF THE INVENTION

Catheters formed of a biocompatible plastics material are sometimes implanted in patients to relieve various symptoms and/or to assist in medical procedures. For example, central venous catheters have been implanted into a patient's vein during vascular surgery. One problem associated with such implanted catheters, however, is that a fibrin sheath (which is a deposit of fibrin and platelets) may form on the implanted catheter, initially at the entrance site into the vein and then along the length of the catheter. While it usually takes weeks to months for the fibrin sheath to form, it has been reported to form in as little as 24–48 hours following implant.

The fibrin sheath can cause catheter dysfunction, usually being manifested by the physician being able to infuse through, but not to aspirate from, the catheter. Intraluminal urokinase may then be administered several times to exclude the possibility of intraluminal clotting. If intraluminal urokinase treatment is ineffective, fluoroscopy may then be performed to allow the physician to evaluate catheter tip location and to obtain evidence of fibrin sheath formation.

Once the presence and extent of the fibrin sheath have been identified, the physician must take the necessary steps to remove the sheath from the implanted catheter. While it is conceivable that the implanted catheter may be removed and replaced surgically, it is more desirable for the fibrin sheath to be removed without surgical removal of the implanted catheter.

Presently, there are basically two approaches which may be employed without removal of the implanted catheter. The first approach involves introducing percutaneously a gooseneck snare (e.g., a snare device generally disclosed in U.S. Pat. No. 5,171,233 to Amplatz et al, the entire content of which is incorporated expressly hereinto by reference) into the patient's groin area. The snare is then advanced through the patient's femoral vein to the catheter implant site, at which time it is manipulated so that the snare encircles the distal end of the implanted catheter so that the fibrin sheath may be stripped therefrom. While the fibrin sheath which is stripped from the distal end of the implanted catheter travels to the patient's lung, surgical removal has been shown to result in embolization as well.

Another technique that has been employed to strip fibrin sheaths from the distal ends of implanted catheters is to introduce a J-tipped wire intraluminally through the implanted catheter. Rotation of the J-tipped wire about the distal end of the implanted catheter will thus strip a portion of the fibrin sheath therefrom. While this technique is advantageous since the implanted catheter serves as a guide passageway (i.e., separate incisions to access the femoral vein are unnecessary), the J-tipped wire is typically only capable of removing less than all of the fibrin sheath from the implanted catheter due to its size limitations.

What has been needed in this art, therefore, is a medical device which is capable of being guided intraluminally through an implanted catheter, but which is capable of removing substantially all of the fibrin sheath that may have formed at the catheter's distal end. It is towards fulfilling such a need that the present invention is directed.

Broadly, the present invention is embodied in medical devices having a snare loop for removing patient-internal material from an implanted catheter (e.g., a fibrin sheath which may form at the distal end of a venous catheter) which may be inserted intraluminally through the catheter during a medical procedure, the snare loop being capable of retroflexing in a proximal direction when extended beyond the distal end of the catheter so that it encircles the implanted catheter's distal region.

According to one embodiment of the invention, such retroflexing is accomplished by incorporating at least one pair of bend regions in the guide wire which are axially spaced-apart from one another. These bend regions will cause the shape-memory guide wire to flex upon advancement of the device beyond the distal end of the catheter so that the snare loop is capable of retroflexing around the catheter's distal end.

Another embodiment of this invention includes a number of proximally directed struts having one end attached to the distal end of the guide wire. A draw wire extends from the guide catheter and is flexed in a proximal direction so as to be connected to the snare loop which is positionally held by the terminal ends of the struts. When the draw wire is pulled proximally, the struts are moved toward parallel alignment with the guide catheter which, in turn, contracts the snare loop. Advancement of the device and/or withdrawal of the draw wire will therefore allow the contracted snare loop to strip a distal segment of the fibrin sheath from the implanted catheter's terminal end. A membrane may optionally be connected to the struts so that the removed fibrin sheath segment may be captured and removed proximally through the lumen of the implanted catheter.

Further aspects and advantages of this invention will become apparent after careful consideration is given to the following detailed description of the preferred exemplary embodiments thereof.

BRIEF DESCRIPTION OF THE DRAWINGS

Reference will hereinafter be made to the accompanying drawings wherein like reference numerals throughout the various FIGURES denote like structural elements, and wherein.

DETAILED DESCRIPTION OF THE PREFERRED EXEMPLARY EMBODIMENTS

Figure 1:
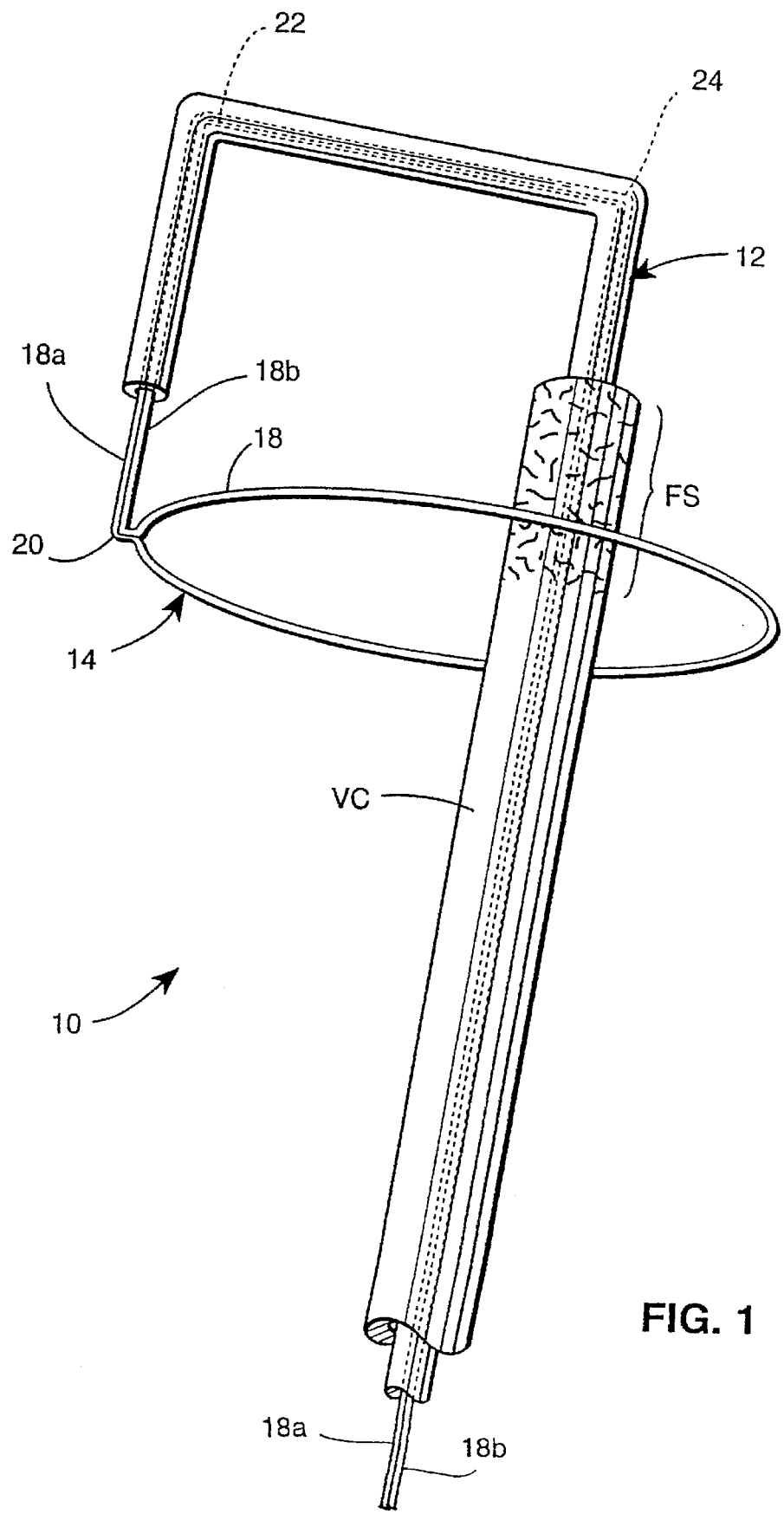
FIG. 1 is a schematic perspective view of one embodiment of a medical snare device according to the present invention.

One preferred embodiment of a medical snare device 10 according to the present invention is shown in accompanying FIG. 1. The snare device 10 is depicted schematically as being positioned intraluminally within a venous catheter VC, it being understood that the distal end region of venous catheter VC will in use be implanted within a patient's vein. The distal end section of the venous catheter VC is depicted in accompanying FIG. 1 as having a fibrin sheath FS extending proximally along the catheter's exterior surface.

The snare device 10 includes a proximal tubular member 12 and a distal loop member 14. The distal loop member 14 is formed into a circular or elliptical snare loop and is preferably constructed of a shape-memory alloy wire 18. The distal loop member 14 is connected integrally to proximal tail wire portions 18a, 18b at bend 20. The proximal tail wire portions 18a, 18b thus extend proximally through the proximal tubular member 12 to a patient-external site where they each can be manipulated by an attending physician. The proximal tubular member 12, on the other hand, extends proximally of the bend 20 to a patient-external site where it also can be manipulated by an attending physician.

Most preferably, the loop member 14 is integral (unitary) with the wire tail portions 18a, 18b and formed from a single, continuous wire element made of shape-memory wire (e.g., NiTi alloy). The particular size of the wire 18 is dependent upon the size of the snare device 10. However, preferably, the size of the wire 18 will nominally be between about 0.005 to about 0.025 inch in diameter and will have a length between about 60 to about 260 cm, with the loop member 14 being formed from the distalmost wire length of about 0.5 to about 5.0 cm.

The bend 20 in the wire 18 is such that the distal loop member 14 extends within a plane at an angle between about 45° to about 135° (preferably about 90°) relative to the longitudinal axis of the proximal tubular member 12. According to the present invention, the wire 18 includes, in addition to bend 20, at least two other bends 22, 24 located proximally of the bend 20 at spaced-apart axial locations along the wire tails 18a, 18b. The functional purpose of these bends 22, 24 will become evident from accompanying FIGS. 2A–2C.

Figure 2C:
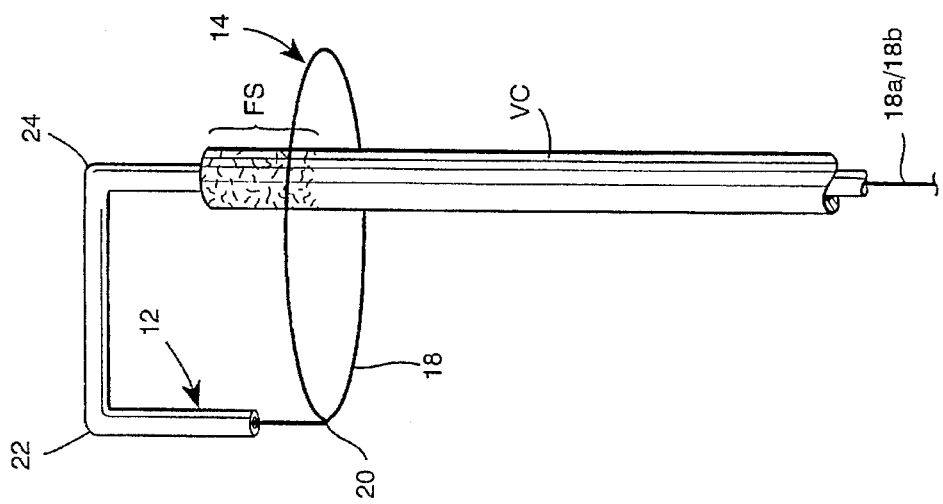
FIGS. 2A–2C schematically show in side elevation views the sequence by which the device of FIG. 1 may be positioned relative to the distal end of the implanted catheter.
Figure 2B:
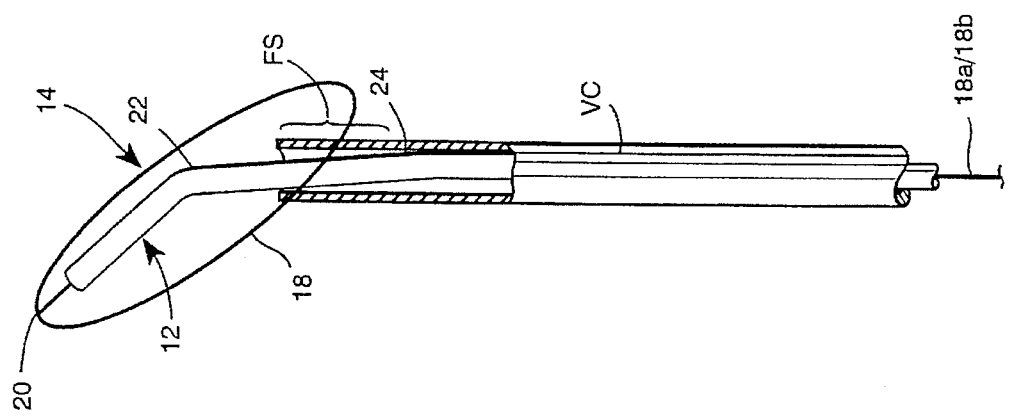
Figure 2A:
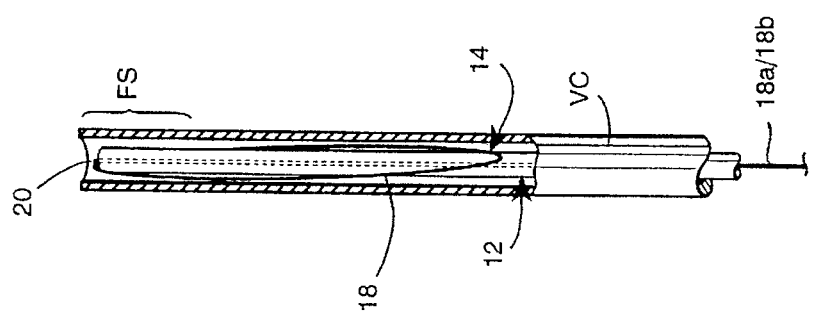

In this regard, accompanying FIG. 2A shows the snare device 10 intraluminally inserted within the venous catheter VC. When the loop member 14 has been advanced beyond the venous catheter's distal end and is thus no longer confined by the venous catheter's lumen, the loop member 14 will assume an angular orientation relative to the longitudinal axis of the proximal tubular member 12 due to the presence of bend 20 in the shape-memory Alloy wire 18. Continued advancement of the proximal tubular member 12 beyond the venous catheter's distal end will thereby allow the bend 22 to emerge from the confinement of the venous catheter's lumen. As a result, as shown in FIG. 2B, the loop member 14 will be encouraged to encircle the elongate axis of the venous catheter VC, even though the loop member 14 will still be angularly oriented relative to the elongate axis of the venous catheter VC.

Upon emergence of the bend 24 from the confines of the venous catheter lumen, however, a bias force will be exerted upon the bend 20 causing the loop member 14 to in essence retroflex in a proximal direction so that the loop member 14 encircles the distal end section of the venous catheter VC and is disposed in a plane which is substantially normal to the venous catheter's elongate axis as shown in FIG. 2C (i.e., disposed at an angle between about 45° to about 135°, and preferably about 90°, relative to the elongate axis of the venous catheter VC). This beneficial retroflexing thus positions the loop member 14 in an encircling relationship to the fibrin sheath FS at the venous catheter's distal end—that is, the plane of the loop member 14 is disposed substantially transversely relative to the longitudinal axis of the venous catheter VC and, moreover, is disposed proximally of the bend 24. By manipulating the wire tails 18a, 18b and/or the proximal tubular member 12, therefore, the attending physician may constrict the loop member 14 so that it grasps the exterior surface of the venous catheter VC in the region of the fibrin sheath FS. Movement of the proximal tubular member 12 in a distal direction, therefore, will allow the constricted loop member 14 to strip the fibrin sheath FS from the distal end of the venous catheter VC.

Figure 3:
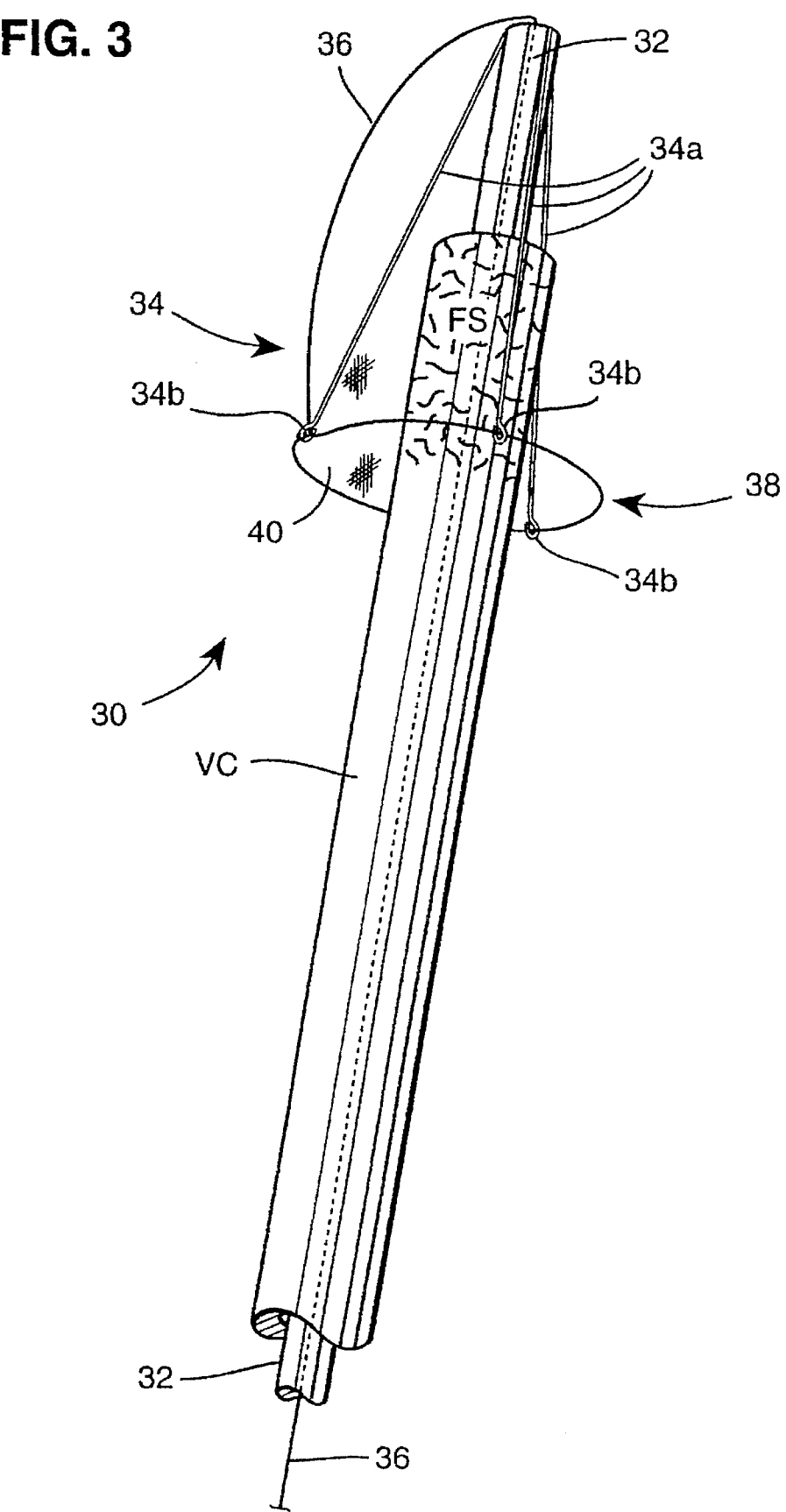
FIG. 3 is a schematic perspective view of another embodiment of a medical snare device according to the present invention.

Another embodiment of a snare device 30 is depicted schematically in accompanying FIG. 3 as including a proximally extending tubular member 32 which includes at its distal end a snare assembly 34. The snare assembly 34 includes a number of struts 34a which extend proximally of the tubular member's distal end. Although three equidistantly separated struts 34a are shown in FIG. 3, it will be appreciated that more/less numbers of such struts 34a may be employed.

Each of the struts 34a has one end attached to the tubular member 32 near the latter's distal end (e.g., via biocompatible adhesive, thermal welding or the like) and an opposite end which terminates in an eyelet 34b. A draw wire 36 extends through the lumen of the tubular member 32 and is threaded through each of the eyelets 34b. The terminal end of the draw wire 36 is, however, affixed to that one of the eyelets 34b through which the wire 36 is first threaded (e.g., the left-most eyelet as viewed in FIG. 3). The terminal portion of the draw wire 36 threaded through the eyelets 34b will thus form a snare loop 38 which encircles the distal end of the venous catheter VC.

Figure 4E:
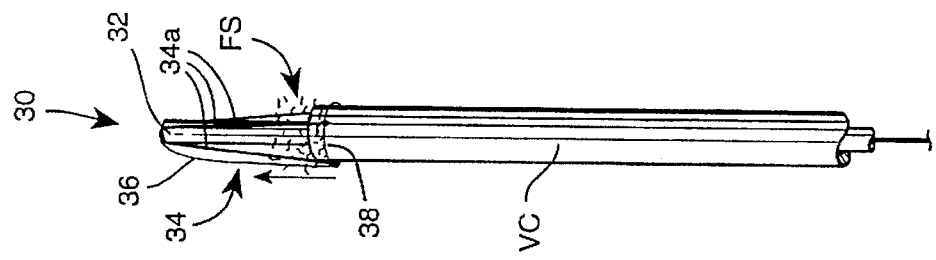
FIGS. 4A–4E schematically show in side elevation views the sequence by which the device of FIG. 3 may be positioned relative to the distal end of the implanted catheter.

In use, the draw wire will initially be pulled proximally so that the struts 34a are each positioned in substantially parallel alignment with the elongate axis of the tubular member 32. In this state, the snare assembly 34 will be of minimal profile so as to be capable of being inserted intraluminally through the venous catheter VC. When the snare assembly 34 has been moved distally beyond the end of the venous catheter VC (as shown in FIG. 4A), the pull wire 36 may be advanced distally to allow the struts 34a formed of shape-memory Alloy wire to deflect outwardly relative to the tubular member 32 as shown in FIG. 4B. Thereafter, as shown in FIG. 4C, proximal movement of the tubular member 32 relative to the venous catheter Vc will cause the snare loop 38 to encircle the distal end of the venous catheter VC on which the fibrin sheath FS has formed.

Figure 4D:
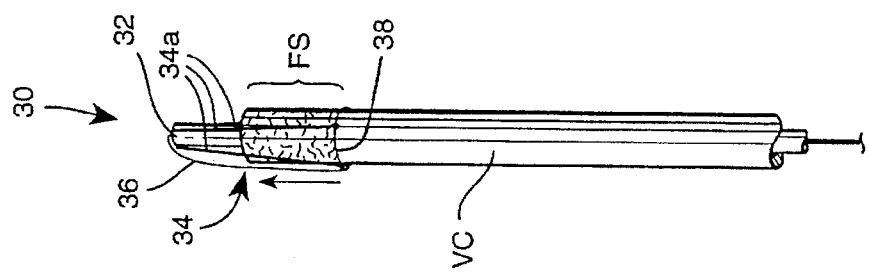
Figure 4C:
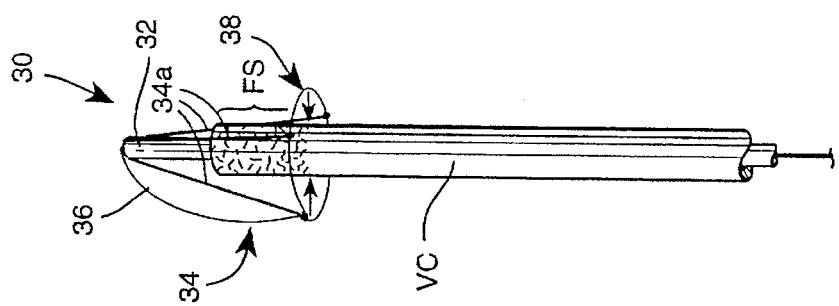
Figure 4B:
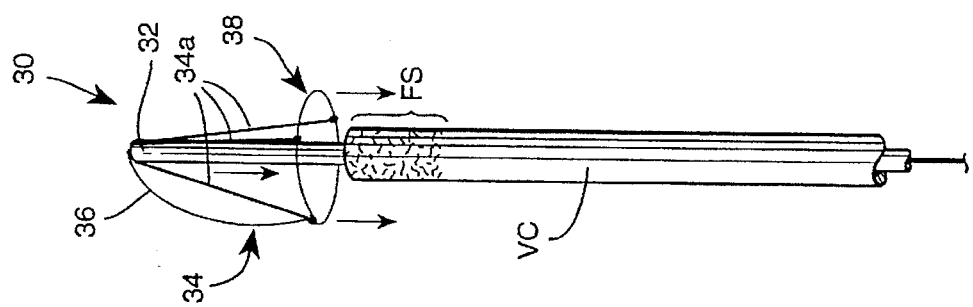
Figure 4A:
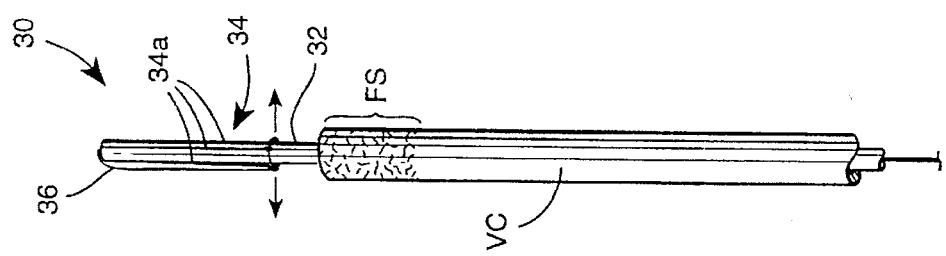

The physician may then move the pull wire 36 in a proximal direction which will cause the snare loop 38 to constrict about the exterior surface of the venous catheter VC as shown in FIG. 4D. Thus, distal advancement of the tubular member 32 while the snare loop 38 is in such a contracted state will cause the snare loop 38 to strip the fibrin sheath FS from the distal end of the venous catheter VC as shown in FIG. 4E. In order to facilitate removal of the fibrin sheath (e.g., via aspiration through the venous catheter's lumen), the snare assembly 34 may optionally be provided with a flexible membrane 40 attached to the struts 34a. The membrane 40 will thus form a generally conical-shaped cover over the struts 34a which is open at the snare loop 38.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A medical snare device for removing patient-internal material during a medical procedure comprising:

an elongate tubular member;

a flexible wire disposed within said tubular member and having a distal end portion which is capable of being extended beyond a terminal end of said tubular member; and a snare loop attached to said distal end portion of said wire, wherein said wire is formed of a shape-memory metal alloy and includes a plurality of axially separated bends to cause said wire to retroflex from a deformed condition wherein said wire is aligned with and confined by said tubular member, and into a non-deformed condition wherein said distal end portion of said wire is flexed in a proximal direction such that the snare loop encircles a distal region of said tubular member in response to extension of said distal end portion of said wire beyond said terminal end of said tubular member.

2. A medical snare device as in claim 1, wherein said flexible wire includes:

at least one bend joining said snare loop to said wire distally of said terminal end of said tubular member to cause said snare loop to be oriented within a plane disposed at an angle with respect to said elongate tubular member, and at least two other bends axially spaced-apart from one another proximally of said at least one bend, said at least two other bends causing said snare loop to be retroflexed over and around said terminal end of said tubular member.

3. A medical snare device for removing patient-internal material from a distal end region of a catheter during a medical procedure comprising:

an elongate tubular member sized so as to be insertable through the catheter;

a flexible wire disposed within said tubular member and having a distal end portion which is capable of being extended beyond a terminal end of said tubular member;

a snare loop attached to said distal end portion of said wire; and a number of proximally extending struts each formed of a shape memory alloy and having a distal end attached to said terminal end of said tubular member and a proximal end which includes an eyelet positioned proximally of said terminal end of said tubular member; wherein said flexible wire is threaded through said eyelets of said struts to form said snare loop, and wherein said struts are resiliently moveable from a deformed condition, wherein said struts are aligned with said tubular member, and into a non-deformed condition, wherein said struts extend outwardly so as to expand the snare loop so that relative movement between said tubular member and said catheter causes the snare loop to encircle the distal end region of the catheter.

4. A medical snare device as in claim 3, wherein a distal end of said wire is attached to one of said eyelets such that movement of the flexible wire in a proximal direction causes said snare loop to constrict.

5. A medical snare device as in claim 3 or 4, further comprising a membrane cover attached to said struts so as to form a generally conical shaped enclosure extending from snare loop to said terminal end of said tubular member.

6. A medical snare device adapted to being advanced intraluminally through a patient-internal catheter so as to remove biological material at a distal end thereof, said snare device comprising:

a elongate tubular member;

a flexible wire formed of a shape-memory alloy disposed within said elongate tubular member and having a distal portion thereof formed into a loop;

said loop being joined to a remaining proximal section of said flexible wire by at least one bend positioned distally of a terminal end of said elongate tubular member so as to orient said loop within a plane at an angle relative to said elongate tubular member;

said flexible wire having at least two other bends formed at axially spaced-apart locations proximally of said terminal end of said tubular member to allow said loop to retroflex proximally over and around the distal end of said patient-internal catheter in response to said loop being extended beyond said terminal end of said tubular member, whereby manipulation of the snare loop removes biological material therefrom.

7. A snare device as in claim 1 or 6, wherein said snare loop is oriented at an angle between about 45° to about 135° relative to said tubular member.

8. A snare device as in claim 7, wherein said snare loop is oriented at an angle of about 90° relative to said tubular member.

9. A snare device as in claim 1 or 7, wherein said snare loop and said flexible wire are integral with one another and formed from a single continuous wire.

10. A medical snare device adapted to being advanced intraluminally through a patient-internal catheter so as to remove biological material at a distal end thereof, said snare device comprising:

an elongate tubular member having a terminal end; and a snare assembly disposed at said terminal end of said elongate tubular member, said snare assembly including, (i) at least one pair of flexible wire struts each formed of a shape-memory alloy and having a distal end affixed to said terminal end of said elongate tubular member and an opposite end positioned proximally of said distal end; and (ii) a pull wire intraluminally extending through said tubular member and having a distal section which extends beyond said terminal end of said tubular member, said distal section being flexed proximally and connected to said opposite ends of said wire struts so as to form a snare loop thereat which encircles said tubular member at a location proximally of said catheter distal end and allows said snare loop to be constricted in response to proximal movement of said pull wire within said tubular member, whereby constriction of said snare loop about said distal end of said catheter and distal movement of said snare tubular member relative to said catheter strips said biological material from said catheter distal end.

11. A snare device as in claim 10, wherein said snare assembly includes eyelet formed at said opposite end of each of said struts, said distal section of said pull wire being threaded through said eyelets.

12. A snare device as in claim 11, wherein a terminal end of said distal pull wire section is affixed to one of said eyelets.

13. A snare device as in claim 11 or 12, wherein said snare assembly further includes a membrane attached to said struts and forming a generally conical shaped enclosure about said terminal end of said tubular member which is open at said snare loop.

14. A procedure for removing a fibrin sheath from a distal end segment of a venous catheter comprising:

intraluminally advancing a snare device having a distal snare loop through the venous catheter until said snare loop is positioned distally of said distal end segment of said venous catheter so as to be unconfined thereby;

manipulating said snare device to cause said snare loop to retroflexibly encircle said distal end segment of said venous catheter; and then distally advancing said snare device while said snare loop thereof is in said encircled relationship with said distal end segment of said venous catheter to cause said snare loop to strip said fibrin sheath therefrom.

15. A procedure as in claim 14, which includes using a snare device having a snare loop joined to a shape-memory wire at one bend located distally of a terminal end of a tubular member in which the wire is positioned, and at least two other axially spaced-apart bends formed in said wire proximally of said at least one bend and said terminal end of said tubular member, wherein said snare device is advanced beyond said distal end segment of said venous catheter until said at least two other wire bends are unconfirmed by said venous catheter to thereby allow said snare loop to retroflex proximally and encircle said distal end segment of said venous catheter.

16. A procedure as in claim 14, wherein said snare device includes a snare assembly which includes at least one pair of proximally extending struts each formed of a shape-memory alloy and having one end attached to a terminal end of an elongate tubular member, and a pull wire extending through said tubular member and attached to ends of said struts opposite said one ends thereof to form said snare loop which encircles said tubular member, said procedure comprising:

(i) advancing said tubular member intraluminally through said venous catheter with said struts disposed in substantial parallel alignment with said elongate tubular member until said snare assembly extends beyond said distal end segment thereof;

(ii) allowing the struts to deflect outwardly from said tubular member and expand the snare loop by virtue of inherent shape-memory characteristic of the struts in response to extension of the snare assembly beyond the distal end segment of the venous catheter;

(iii) retracting said tubular member until said expanded snare loop encircles said distal end segment of said venous catheter;

(iv) pulling on said pull wire to constrict said snare loop against said distal end segment of said venous catheter; and then (v) effecting relative axial movement to occur between said tubular member and said snare loop while maintaining constriction of said snare loop against said distal end segment of said venous catheter to cause said snare loop to strip said fibrin sheath therefrom.

17. A procedure as in claim 16, which further includes capturing said stripped fibrin sheath in a membrane enclosure attached to said struts.

* * * * *